US006846462B2

(12) United States Patent
Stanley, III

(10) Patent No.: US 6,846,462 B2
(45) Date of Patent: Jan. 25, 2005

(54) INCENSE BURNER

(76) Inventor: Virgil E. Stanley, III, 5860 N. Michigan Rd., Indianapolis, IN (US) 46228

(*) Notice: Subject to any disclaimer, the term of this patent is extended or adjusted under 35 U.S.C. 154(b) by 223 days.

(21) Appl. No.: 10/173,189

(22) Filed: Jun. 17, 2002

(65) Prior Publication Data
US 2003/0231991 A1 Dec. 18, 2003

(51) Int. Cl.[7] .................................................. A62B 7/08
(52) U.S. Cl. ........................ 422/126; 422/120; 431/356
(58) Field of Search ................................ 422/120, 126, 422/4; 431/356

(56) References Cited

U.S. PATENT DOCUMENTS

| 1,530,103 A | 3/1925 | Booth |
| 1,851,742 A | 3/1932 | Vinther |
| 1,969,756 A | 8/1934 | Lowell |
| 2,131,460 A | 9/1938 | White |
| 4,099,916 A | 7/1978 | Gardner et al. |
| 4,178,346 A | 12/1979 | Allen et al. |
| 4,198,375 A | 4/1980 | Rogers |
| 4,237,097 A | 12/1980 | McDuffie |
| 4,324,763 A | 4/1982 | Jarman |
| 4,347,217 A | 8/1982 | Radkins et al. |
| 5,563,981 A | 10/1996 | Hsiao |
| D395,846 S | 7/1998 | Taylor |
| 6,061,950 A | 5/2000 | Carey |

Primary Examiner—Krisanne Jastrzab
(74) Attorney, Agent, or Firm—Coats & Bennett, P.L.L.C.

(57) ABSTRACT

An incense burner is provided with an upper compartment comprising a bottom, surrounding side wall structure, and an open top. An array of openings is provided in the bottom that permits air to move upwardly through the bottom into a burning chamber defined above the bottom and interiorally of the surrounding side wall structure. A series of legs extends downwardly from the bottom to where they join a base. An open space is defined between the bottom and the base. In addition, there is provided a series of side openings that are formed between the bottom and the base, and between the respective legs. This enables air to move inwardly through the side openings into the space between the bottom and the base, and therefrom upwardly through the array of openings in the bottom into the burning chamber of the incense burner.

15 Claims, 6 Drawing Sheets

INCENSE BURNER

FIELD OF THE INVENTION

The present invention relates to incense burners.

BACKGROUND OF THE INVENTION

Incense burners are well-known and appreciated in the art. As a general rule, incense burners include a burning chamber for receiving and holding incense while the incense is being burned. One of the major disadvantages of incense burners of the prior art, is that conventional incense burners are not designed to burn efficiently and cleanly. For example, many incense burners include a generally closed burning chamber except for an open top. These types of incense burners do not generally provide a sufficient oxygen supply to the burning chamber to enable the device to burn cleanly and efficiently.

SUMMARY OF THE INVENTION

The present invention relates to an incense burner having a base and a bottom spaced above the base. A surrounding side wall structure extends upwardly from the base to an open top that is formed above the bottom. At least one opening is formed in the bottom that permits air to flow into a burning chamber defined above the bottom and interiorally of the surrounding side wall structure. At least one opening is formed in the side wall structure between the base and the bottom, permitting air to enter the side opening and move upwardly therefrom through the opening formed in the bottom.

In one embodiment, the incense burner includes an upper burning unit having a bottom, a surrounding side wall structure and an open top disposed opposite the bottom. The bottom, surrounding side wall structure, open top form a burning chamber for receiving and holing incense. Further, the bottom includes an array of openings that permits air to flow upwardly through the bottom into the burning chamber. A series of legs extend downwardly from the bottom to where the legs join a base, and wherein the base is spaced below the bottom do as to define an open area between the base and the bottom. There is provided a series of side openings between the base and the bottom, and between the respective legs such that air may flow through the side openings into the space between the base and the bottom, and upwardly therefrom through the openings in the bottom into the burning chamber.

Other objects and advantages of the present invention will become apparent and obvious from a study of the following description and the accompanying drawings which are merely illustrative of such invention.

DESCRIPTION OF EXEMPLARY EMBODIMENT

Figure 1:
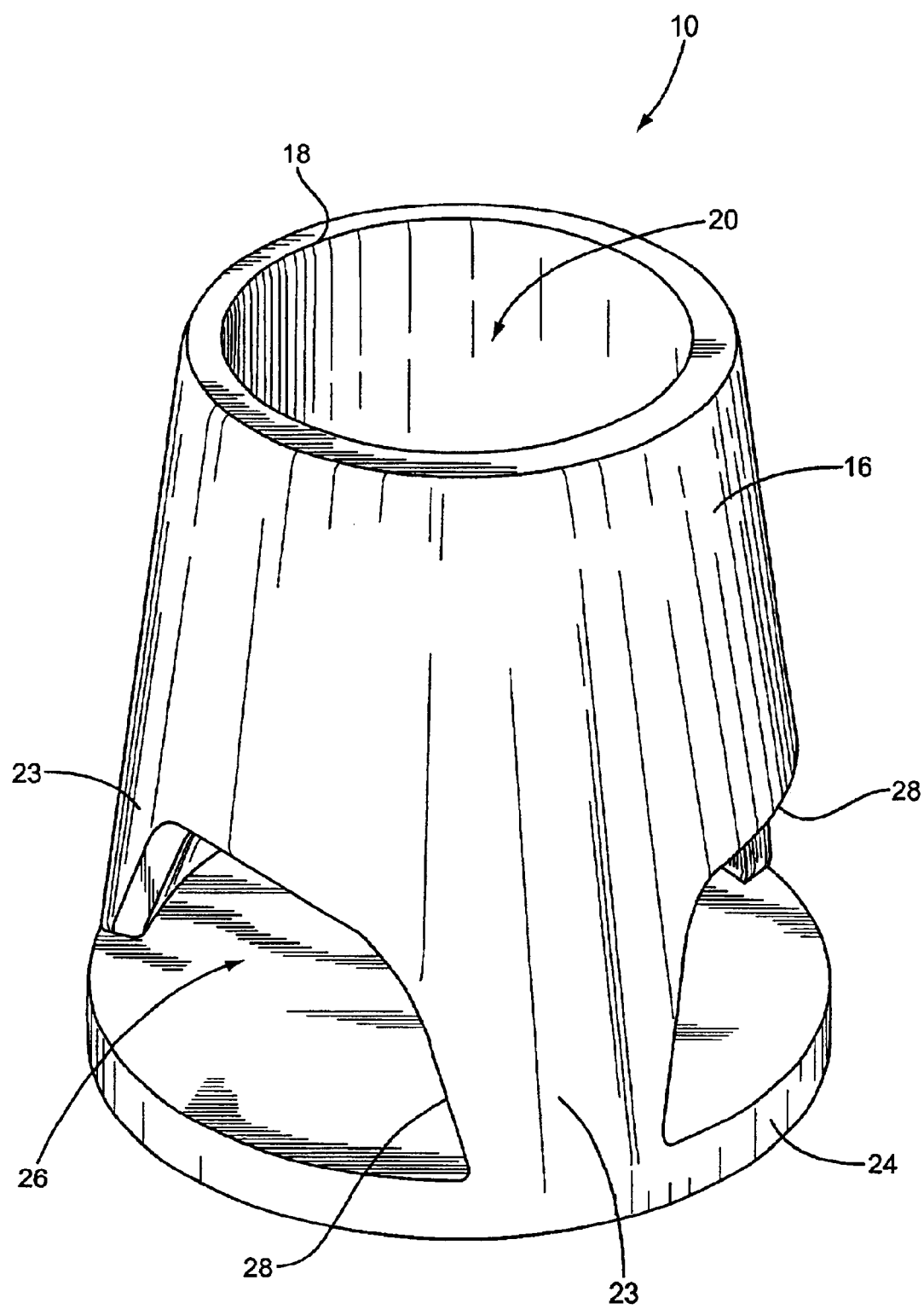
FIG. 1 is a perspective view of the incense burner.
Figure 1A:
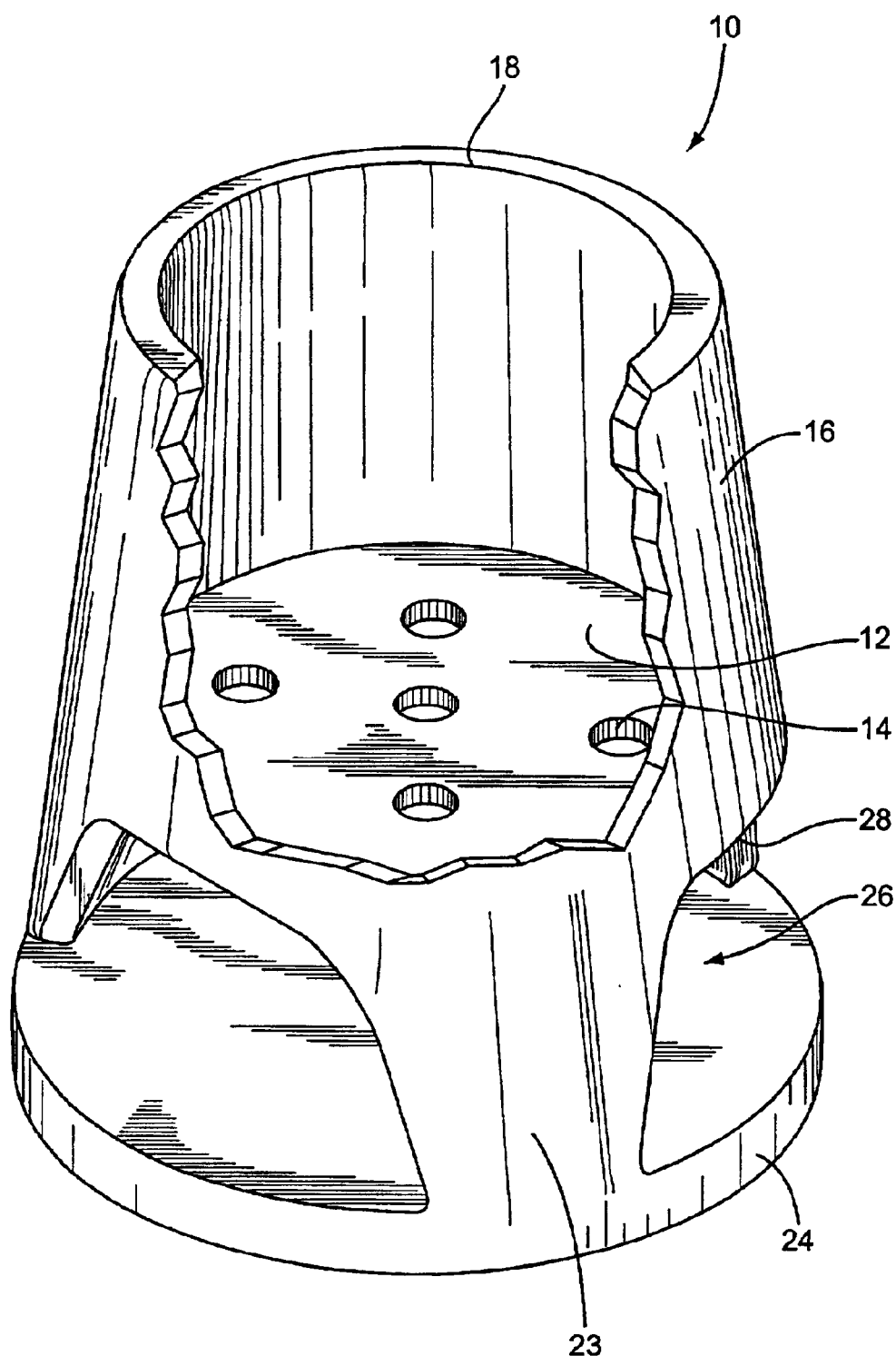
Figure 2:
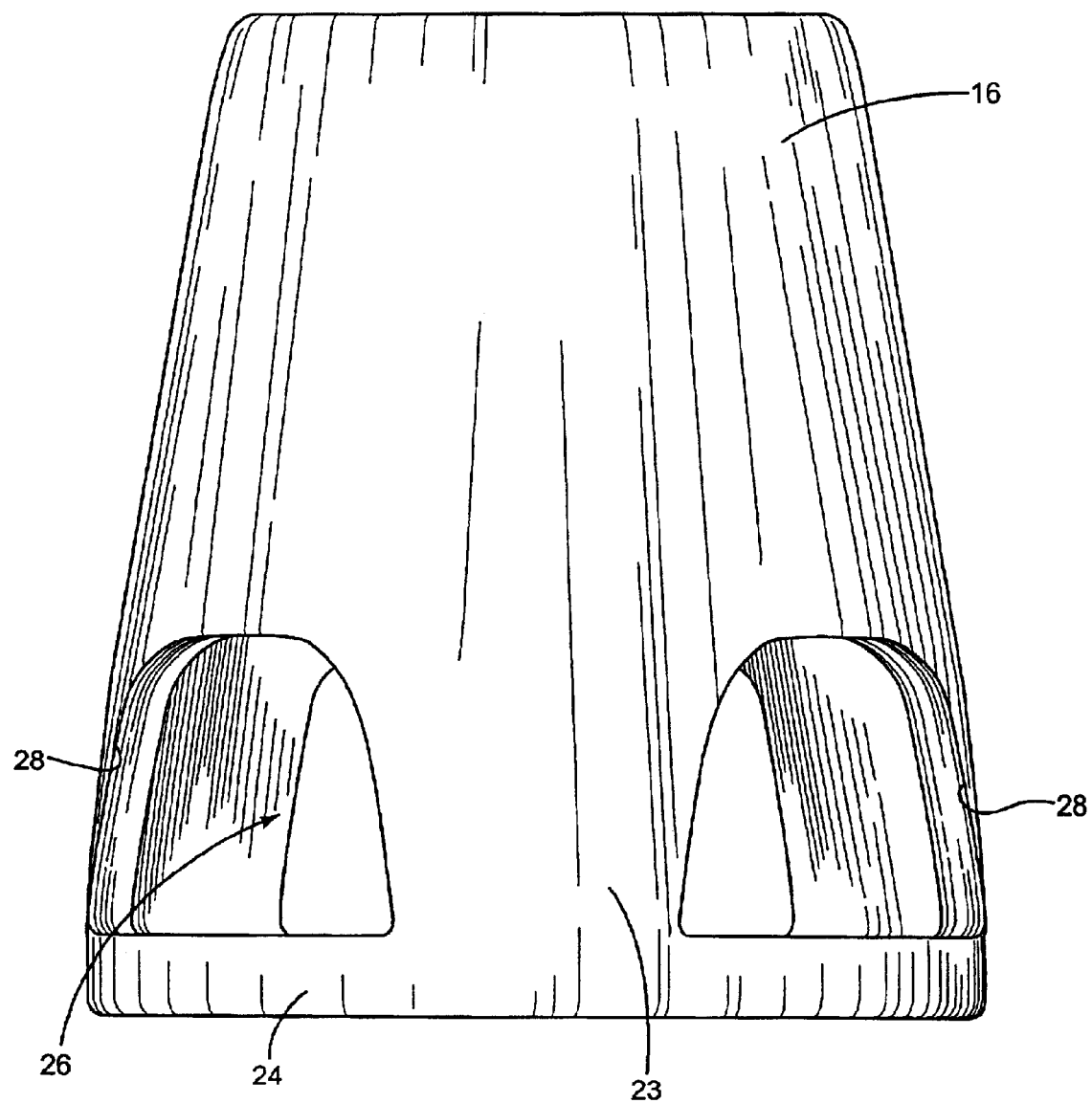
FIG. 2 is a front elevational view of the incense burner.
Figure 3:
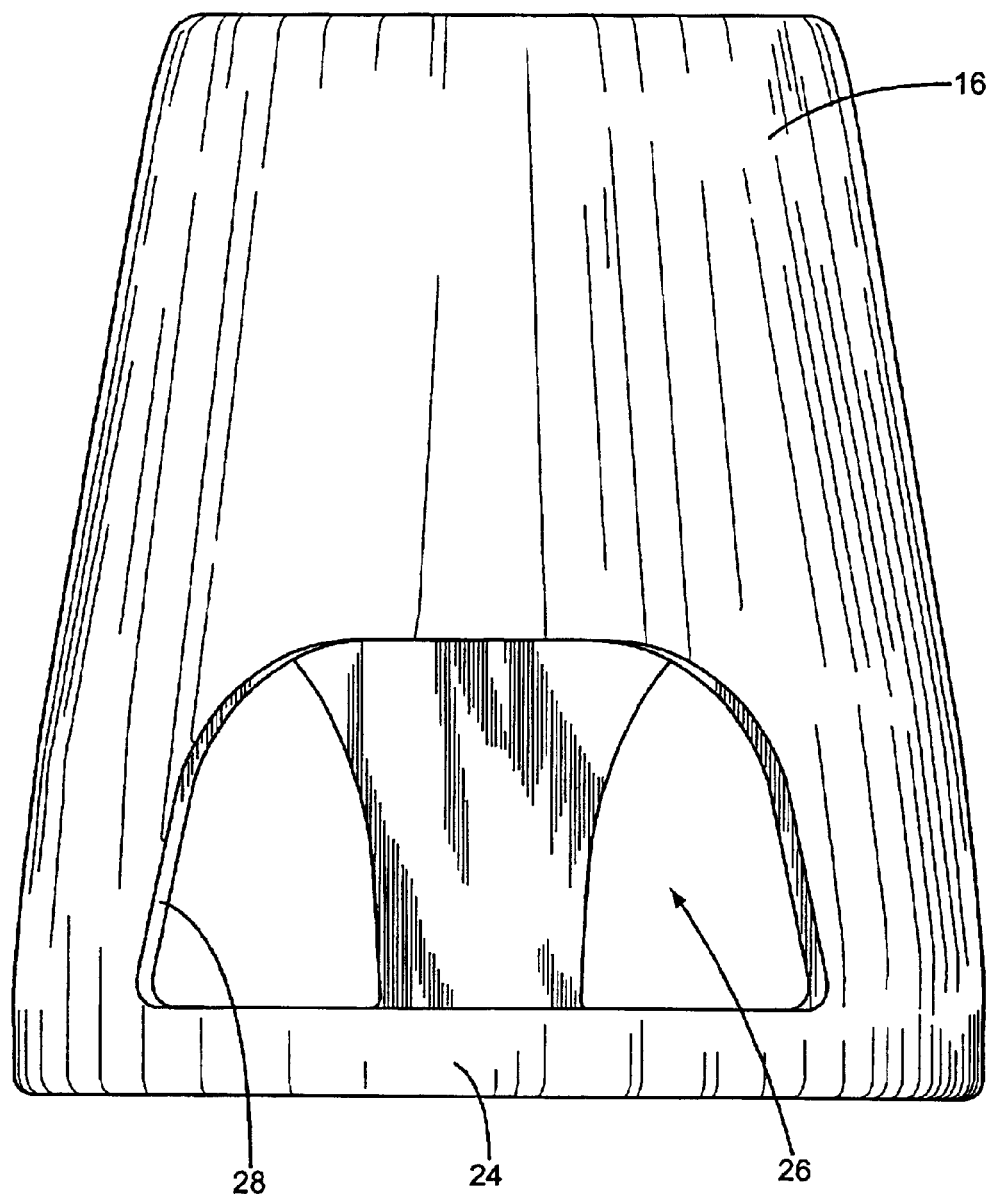
FIG. 3 is a rear elevational view of the incense burner.
Figure 4:
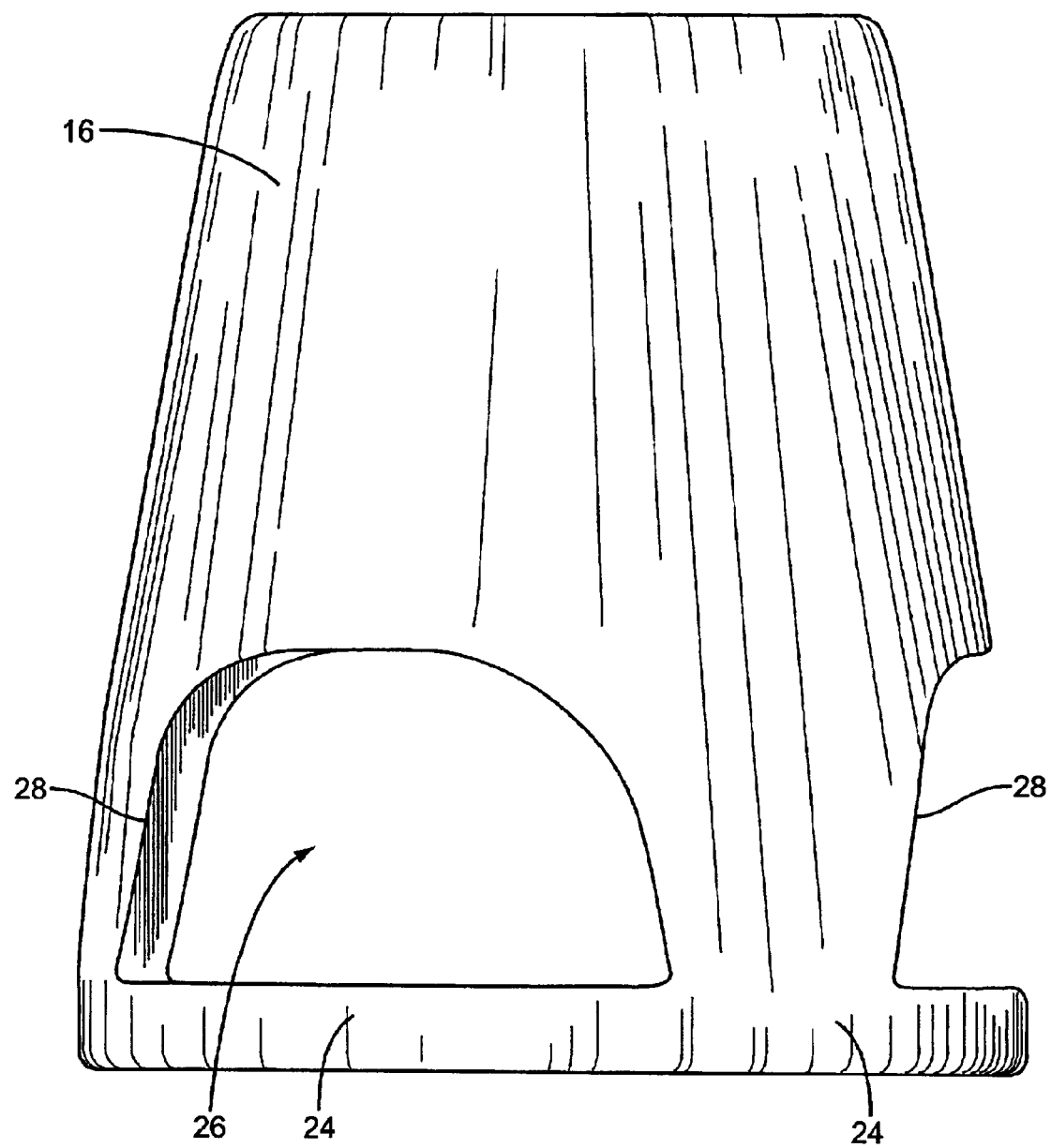
FIG. 4 is a side elevational view of the incense burner.
Figure 5:
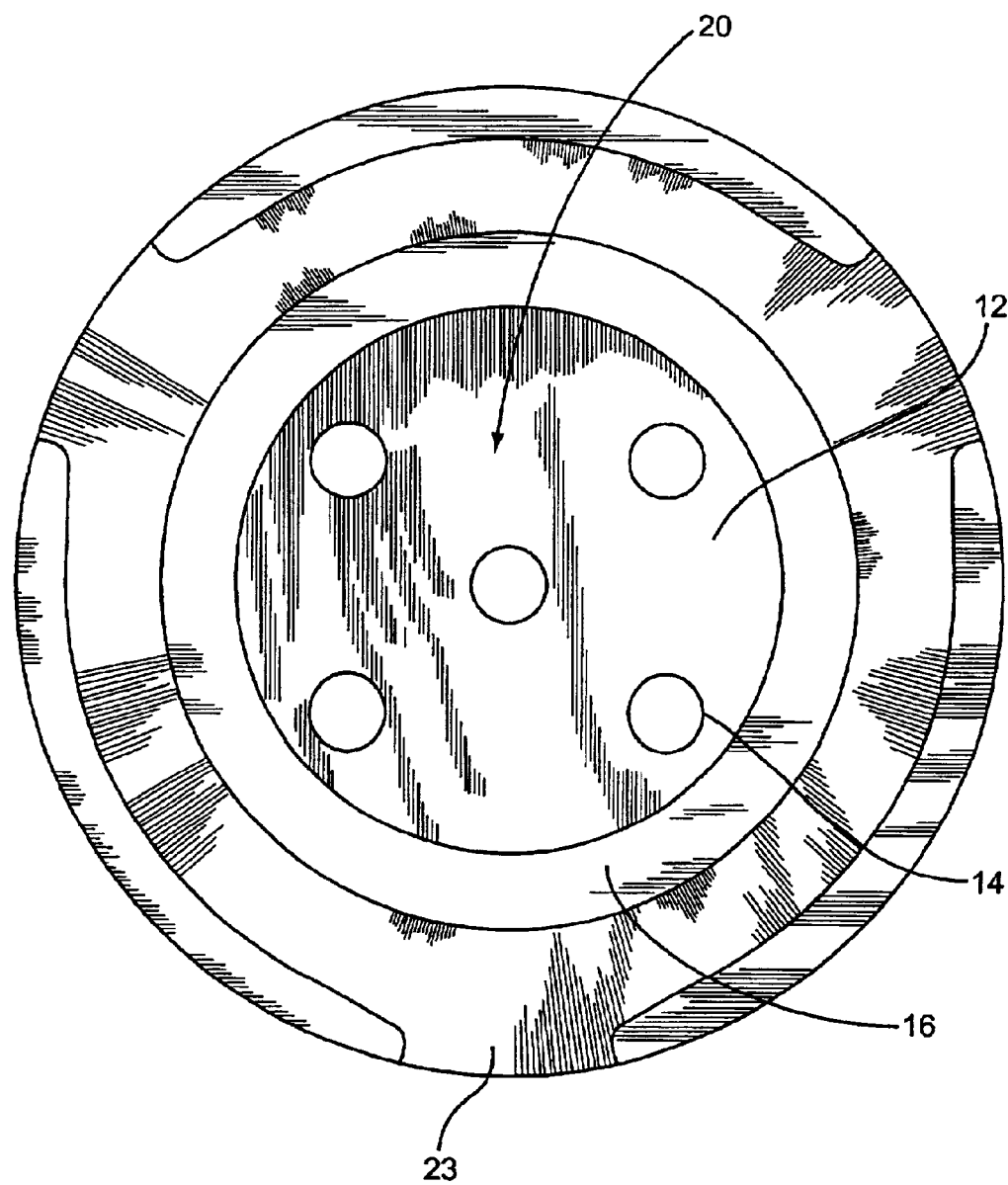
FIG. 5 is a top plan view of the incense burner.

With further reference to the drawings, the incense burner of the present invention is shown therein and indicated generally by the numeral 10. As will be appreciated from subsequent portions of this disclosure, the incense burner 10 is adapted to receive and hold incense and to provide a burning chamber where the incense can be burned.

Viewing the incense burner in more detail, the same includes an upper unit that is made up of a bottom 12 having an array of openings 14 formed therein. Extending upwardly from the bottom 12 is a surrounding side wall structure 16. An open top 18 is formed above the bottom 12. Defined within the surrounding side wall structure 16 between the bottom 12 and the open top 18 is a burning chamber indicated generally by the numeral 20.

As seen in the drawings, the surrounding side wall structure 16 is generally curved and tapers inwardly as the wall structure extends upwardly from the bottom 12 towards the open top 18.

Extending downwardly form the bottom 12 is a series of legs 22. Legs 22 extend from the bottom 12 downwardly to where they join a base 24. Base 24 assumes a generally round configuration. As seen in the drawings, the bottom 12 is spaced above the base 24. Therefore, there is an area or space defined between the bottom 12 and the base 24. The upper surface of the base 24 serves to catch and hold ashes that may drop from the burning chamber 20 through the array of openings 14 formed in the bottom 12.

Formed between the legs 22 and the base 24 are a series of side openings 28. Side openings 28 open directly to the open area or space 26 found between the bottom 12 and the base 24. In any event, it is seen that the side openings 28 are uniformly spaced and each such opening is bound by a portion of the base 24, portions of adjacent legs 22, and a portion of the surrounding side wall structure 16. In the case of the embodiment illustrated herein, each side opening 24 includes an upper segment that assumes a generally arcuate shape, while the base of the opening generally curves with the base as best illustrated in FIG. 1.

In the embodiment illustrated herein, the entire shape of the incense burner 10 assumes a generally frustro-conical shape. That is, the base 24 is of a greater diameter than the top portion of the incense burner, and the wall structure, including the legs, tapers inwardly from the base 24 upwardly.

One of the advantages of the incense burner of the present invention lies in its ability to direct an adequate supply of air and oxygen to the burning chamber 12. That is, air tends to be drawn into the side openings 28 and into the open area or space 26 disposed between the bottom 12 and the base 24. From there, the air and oxygen tends to rise and move upwardly through the array of openings 14 into the burning chamber 20. When incense are being burned in the burning chamber 20, the movement of air upwardly into the burning chamber 20 via the array of openings 14 tends to facilitate and promote efficient burning.

Although the incense burner 10 has been described in one exemplary embodiment as having a particular shape and wherein features of the incense burner have also been described as assuming particular shapes, it is appreciated that the shape and size of the incense burner as well as the shape and size of various features of the incense burner may vary from one design to another.

The present invention may, of course, be carried out in other specific ways than those herein set forth without departing from the scope and the essential characteristics of the invention. The present embodiments are therefore to be construed in all aspects as illustrative and not restrictive and all changes coming within the meaning and equivalency range of the appended claims are intended to be embraced therein.

What is claimed is:

1. An incense burner comprising:
   a base;
   a bottom spaced above the base;
   a wall structure extending from the base upwardly past the bottom;
   an open top;
   at least one opening formed in the bottom; and
   at least one opening formed in the wall structure between the base and the bottom for permitting air to flow through the opening formed in the wall structure into an area defined between the base and bottom, and through the opening formed in the bottom.

2. The incense burner of claim 1 wherein the opening in the wall structure include at least three equally spaced openings.

3. The incense burner of claim 2 wherein the base includes a generally flat plate and wherein portions of the wall structure extending between the openings formed in the wall structure form at least three legs that extend upwardly from the base.

4. The incense burner of claim 3 wherein the openings formed in the wall structure are formed by the base and a nonlinear edge formed in the wall structure.

5. The incense burner of claim 1 wherein the at least one opening formed in the bottom includes an array of openings formed in the bottom.

6. The incense burner of claim 1 wherein the base forms an area for collecting ashes that drop from the bottom through the at least one opening formed in the bottom.

7. The incense burner of claim 1 wherein the surrounding wall structure is tapered generally inwardly along at least some portions of the wall structure extending from the base to the open top.

8. The incense burner of claim 1 wherein the wall structure assumes a generally frustro-conical shape.

9. An incense burner, comprising: an upper burner unit having a bottom, a surrounding side wall structure, and an open top opposite the bottom; the bottom, surrounding side wall structure, and open top forming a burning chamber for receiving and burning incense; the bottom including an array of holes that permits air to flow upwardly through the openings in the bottom into the burning chamber; a series of legs extending downwardly from the bottom; a base joining the legs and wherein the base is spaced below the bottom so as to define an open area between the base and the bottom; and wherein there is defined a series of side openings between the bottom and base, and between the respective legs such that air may flow through the side openings into the space defined between the bottom and the base and upwardly through the array of openings in the bottom into the burning chamber.

10. The incense burner of claim 9 wherein the side openings formed between the legs include an upper arched segment.

11. The incense burner of claim 9 wherein portions of the side opening formed between the respective legs are bounded by the base.

12. The incense burner of claim 9 wherein the base forms an ash catch for receiving ashes that fall through the openings formed in the bottom.

13. The incense burner of claim 9 wherein the surrounding side wall of the upper compartment is generally tapered inwardly from the bottom towards the open top.

14. The incense burner of claim 9 wherein the open top and base each includes a diameter and wherein the diameter of the open top is less than the diameter of the base.

15. The incense burner of claim 9 wherein there is provided three legs extending between the base and the bottom of the upper compartment and wherein the legs are generally equally spaced.

* * * * *